US010526597B2

(12) United States Patent
DuBridge

(10) Patent No.: US 10,526,597 B2
(45) Date of Patent: Jan. 7, 2020

(54) METHOD OF IMPROVING CHARACTERISTICS OF PROTEINS

(71) Applicant: Full Spectrum Genetics, Inc., Belmont, CA (US)

(72) Inventor: Robert DuBridge, Belmont, CA (US)

(73) Assignee: Full Spectrum Genetics, Inc.

( * ) Notice: Subject to any disclaimer, the term of this patent is extended or adjusted under 35 U.S.C. 154(b) by 210 days.

(21) Appl. No.: 15/555,276

(22) PCT Filed: May 16, 2016

(86) PCT No.: PCT/US2016/032660
§ 371 (c)(1),
(2) Date: Sep. 1, 2017

(87) PCT Pub. No.: WO2016/187101
PCT Pub. Date: Nov. 24, 2016

(65) Prior Publication Data

US 2019/0078081 A1 Mar. 14, 2019

Related U.S. Application Data

(60) Provisional application No. 62/165,173, filed on May 21, 2015.

(51) Int. Cl.
*C40B 30/04* (2006.01)
*C12N 15/10* (2006.01)
(Continued)

(52) U.S. Cl.
CPC .......... *C12N 15/1037* (2013.01); *C07K 1/047* (2013.01); *C07K 16/005* (2013.01); (Continued)

(58) Field of Classification Search
None
See application file for complete search history.

(56) References Cited

U.S. PATENT DOCUMENTS 5,798,208 A 8/1998 Crea
5,830,650 A 11/1998 Crea
(Continued)

FOREIGN PATENT DOCUMENTS

WO WO2016/153838 6/2016
WO WO2016/153838 9/2016
(Continued)

OTHER PUBLICATIONS

Dall'Acqua et al, "Antibody humanization by framework shuffling," Methods, 36(1): 43-60 (2005).
(Continued)

*Primary Examiner* — Christian C Boesen
(74) *Attorney, Agent, or Firm* — Stephen C. Macevicz

(57) ABSTRACT

The invention provides efficient methods for combining single-substitution libraries of nucleic acids that span and encode proteins of interest and for selecting resultant mutant proteins after expression which have improved properties or characteristics. Specifically, the methods comprising synthesizing a single substitution library for each of a plurality of domains of a protein; expressing separately each member of each single substitution library as a pre-candidate protein; selecting members of each single substitution library which encode pre-candidate proteins which exhibit an improvement in the one or more predetermined characteristics to form a selected library; shuffling members or the selected libraries in a PCR to produce a combinatorial shuffled library; expressing members of the shuffled library as candidate proteins; and selecting mutant proteins which have improved properties or characteristics.

14 Claims, 7 Drawing Sheets

Specification includes a Sequence Listing.

(51) Int. Cl.

| | |
|---|---|
| ***C07K 1/04*** | (2006.01) |
| ***C07K 16/00*** | (2006.01) |
| *C40B 10/00* | (2006.01) |
| *C40B 40/02* | (2006.01) |
| *C40B 40/10* | (2006.01) |

(52) U.S. Cl.

CPC ..... *C12N 15/1027* (2013.01); *C12N 15/1058* (2013.01); *C12N 15/1079* (2013.01); *C40B 10/00* (2013.01); *C40B 30/04* (2013.01); *C40B 40/02* (2013.01); *C40B 40/10* (2013.01)

(56) References Cited

U.S. PATENT DOCUMENTS

| | | | |
|---|---|---|---|
| 5,830,721 | A | 11/1998 | Stemmer |
| 6,132,970 | A | 10/2000 | Stemmer |
| 6,444,468 | B1 | 9/2002 | Stemmer |
| 6,576,467 | B1 | 6/2003 | Stemmer |
| 6,649,340 | B1 | 11/2003 | Crea |
| 8,633,139 | B2 | 1/2014 | DuBridge |
| 9,012,369 | B2 | 4/2015 | Crea |
| 2005/0048617 | A1 | 3/2005 | Wu |
| 2006/0228350 | A1 | 10/2006 | Wu |
| 2008/0207459 | A1 | 8/2008 | Karrer |
| 2010/0216975 | A1 | 8/2010 | Wu |
| 2012/0077691 | A1 | 3/2012 | DuBridge |
| 2012/0258866 | A1 | 10/2012 | DuBridge |
| 2013/0288908 | A1 | 10/2013 | Fujino |

FOREIGN PATENT DOCUMENTS

| | | | |
|---|---|---|---|
| WO | WO2016/187101 | A2 | 11/2016 |
| WO | WO2016/187101 | A3 | 11/2016 |
| WO | WO2016/187101 | | 2/2017 |

OTHER PUBLICATIONS

Damschroder et al, "Framework shuffling of antibodies to reduce immunogenicity and manipulate functional and biophysical properties," Mol. Immunol., 44(11): 3049-3060 (2007).

Marks et al, "By-passing immunization: Building high affinity human antibodies by chain shuffling," Nature Biotechnology, 10: 779-783 (1992).

Rajpal et al, "A general method for greatly improving the affinity of antibodies by using combinatorial libraries," Proc. Natl. Acad. Sci., 102 (24): 8466-8471 (2005).

Rozak et al, "Offset recombinant PCR: a simple but effective method for shuffling compact heterologous domains," Nucleic Acids Research, 33(9): e82 (2005).

Stemmer, "DNA shuffling by random fragmentation and reassembly: in vitro recombination for molecular evolution," Proc. Natl. Acad. Sci. 91: 10747-10751 (1994).

Swers et al, "Shuffled antibody libraries created by in vivo homologous recombination and yeast surface display," Nucleic Acids Research, 32(3): e36 (2004).

Swers et al, "Integrated mimicry of B cell antibody mutagenesis using yeast homologous recombination," Mol. Biotechnol., 47(1): 57-69 (2011).

Votsmeier et al, "Femtomolar Fab binding affinities to a protein target by alternative CDR residue co-optimization strategies without phage or cell surface display," mAbs 4(3): 341-348 (2012).

SD1 sdFv Library Design

MKYLLPTAAAGLLLLAAQPAMAQVQLVQSGGGLVQPGGSLRLSCAAS-

CDR1 CDR2

DFDFAAYEMSWVRQAPGQGLEWVAIISHDGIDKYYTDSVKGRFTISR-

CDR3

DNSKNTLYLQMNTLRAEDTATYYCLRLGAVGQGTLVTVSS

Fig. 2A

SD1 CDR Library Shuffling

SD1 Round 2 Rescue

| Phage | 0' Meso | 0' PBS | S/N | 18hr Meso | 18hr PBS | S/N | Fold↓ |
|---|---|---|---|---|---|---|---|
| SD1 WT | 3.40E+05 | 1.10E+05 | 3x | 6.40E+04 | 5.10E+04 | 1.3x | 20x |
| CDR | 2.00E+06 | 1.60E+05 | 12.5x | 1.00E+06 | 3.70E+04 | 27x | 2x |
| Dnase | 2.50E+06 | 2.70E+05 | 9.2x | 5.70E+05 | 6.60E+04 | 8.6x | 4x |

Fig. 2C

SD1 Library Round 3 Rescue

| Library | 0' Meso | 0' PBS | S/N | 48hr Meso | 48hr PBS | S/N | Fold↓ |
|---|---|---|---|---|---|---|---|
| SD1 WT | 9.80E+05 | 4.30E+05 | 2.3x | 1.90E+05 | 1.10E+05 | 1.7x | 12.5x |
| CDR | 1.50E+08 | 4.30E+05 | 349x | 8.90E+07 | 6.70E+04 | 1480x | 1.7x |
| Dnase | 2.40E+07 | 3.40E+05 | 70x | 1.90E+07 | 7.90E+04 | 240x | 1.3x |

Fig. 2D

SD1 CDR Shuffle

| | |
|---|---|
| | amino acid change |
| | selected sequences |
| | shuffled |
| | unshuffled framework |

| | | | CDR1 | | | | | | | | | | | | | | | | | | | CDR2 | | | | | | | | | | | | | | | | | | | CDR3 | | | | | | | | | | SEQ ID NO: |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| SD1_WT | S | D | F | D | F | A | A | Y | E | M | S | W | V | R | Q | A | L | E | W | V | A | I | I | S | H | D | G | I | D | K | Y | Y | T | D | S | V | K | G | R | T | Y | Y | C | L | R | L | G | A | V | G | 8 |
| A07 | S | D | F | D | F | A | A | Y | E | M | A | W | V | R | Q | A | L | E | W | V | A | I | I | S | H | D | G | I | D | K | Y | Y | T | D | S | V | K | G | R | T | Y | Q | C | L | L | L | G | A | V | G | 9 |
| A08 | S | D | F | D | F | A | A | Y | E | M | G | W | V | R | Q | A | L | E | W | V | A | I | I | S | H | D | G | I | D | K | Y | Y | D | D | S | V | K | G | R | T | Y | Q | C | L | R | L | G | A | V | G | 10 |
| B07 | S | D | R | D | F | A | E | Y | E | M | G | W | V | R | Q | A | L | E | W | V | A | I | I | S | H | D | G | I | D | K | Y | Y | D | D | S | V | K | G | R | T | Y | Q | C | L | R | L | G | A | V | G | 11 |
| B08 | S | D | S | D | F | A | A | Y | E | M | A | W | V | R | Q | A | L | E | W | V | A | I | I | S | H | D | G | I | D | K | Y | Y | T | D | S | V | K | G | R | T | Y | Q | C | L | R | L | G | A | V | G | 12 |
| C07 | S | D | F | D | F | A | A | Y | E | M | G | W | V | R | Q | A | L | E | W | V | A | I | I | S | H | D | G | I | D | K | Y | Y | D | D | S | V | K | G | R | T | Y | Q | C | L | R | L | G | A | V | G | 13 |
| C08 | S | G | R | D | F | A | A | Y | E | M | G | W | V | R | Q | A | L | E | W | V | A | I | I | S | H | D | G | I | D | K | Y | Y | D | D | S | V | K | G | R | T | Y | Q | C | L | R | L | G | A | V | G | 14 |
| D08 | S | D | F | D | F | A | A | Y | E | M | A | W | V | R | Q | A | L | E | W | V | A | I | I | S | H | D | G | I | D | K | Y | Y | D | D | S | V | K | G | R | T | Y | Q | C | L | R | L | G | A | V | G | 15 |
| E07 | S | D | F | D | F | A | A | Y | E | M | A | W | V | R | Q | A | L | E | W | V | A | I | I | S | H | D | G | I | D | K | Y | Y | D | D | S | V | K | G | R | T | Y | Q | C | L | R | L | G | A | V | G | 16 |
| E08 | S | D | F | D | F | A | A | Y | E | M | G | W | V | R | Q | A | L | E | W | V | A | I | I | S | H | D | G | I | D | K | Y | Y | D | D | S | V | K | G | R | T | Y | Q | C | L | R | L | G | A | V | G | 17 |
| F07 | S | D | G | D | F | A | A | Y | D | M | S | W | V | R | Q | A | L | E | W | V | A | I | I | S | H | D | G | I | D | K | Y | Y | D | D | S | V | K | G | R | T | Y | Q | C | L | R | L | G | A | V | G | 18 |
| F08 | S | D | F | D | F | A | A | Y | D | M | S | W | V | R | Q | A | L | E | W | V | A | I | I | S | H | D | G | I | D | K | Y | Y | T | S | S | V | K | G | R | T | Y | Q | C | L | R | L | G | A | V | G | 19 |
| G07 | S | D | F | D | F | A | A | Y | I | M | S | W | V | R | Q | A | L | E | W | V | A | I | I | S | H | D | G | I | D | K | Y | Y | A | D | S | V | K | G | R | T | Y | Q | C | L | R | L | G | A | V | G | 20 |
| G08 | S | D | F | D | F | A | A | Y | D | M | S | W | V | R | Q | A | L | E | W | V | A | I | I | S | H | D | S | I | D | K | Y | Y | T | D | S | V | K | G | R | T | Y | Y | C | L | K | L | G | A | V | G | 21 |
| H07 | S | D | F | D | F | A | A | Y | E | M | A | W | V | R | Q | A | L | E | W | V | A | I | I | S | H | D | G | I | D | K | Y | Y | T | R | S | V | K | G | R | T | Y | Q | C | L | L | L | G | A | V | G | 22 |
| H08 | S | D | F | D | F | A | T | Y | E | M | G | W | V | R | Q | A | L | E | W | V | A | I | I | S | H | D | G | I | D | K | Y | Y | T | E | S | V | K | G | R | T | Y | Q | C | L | S | L | G | A | V | G | 23 |

Fig. 2E

SD1 DNase1 Shuffle

| | |
|---|---|
| | amino acid change |
| | selected sequences |
| | shuffled |
| | unshuffled framework |

CDR1 CDR2 CDR3

| | | | | | | | | | | | | | | | | | | | | | | | | | | | | | | | | | | | | | | | | | | | | | | | | | | | SEQ ID NO: |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| A11 | S | D | F | T | F | A | A | Y | I | M | G | W | V | R | Q | A | L | E | W | V | A | I | I | S | H | D | G | I | D | K | Y | Y | T | D | S | V | K | G | R | T | Y | Q | C | L | Q | L | G | A | V | G | 24 |
| A12 | S | D | F | E | F | A | A | Y | I | M | A | W | V | R | Q | A | L | E | W | V | A | I | I | S | H | D | G | I | D | K | Y | Y | T | D | S | V | K | G | R | T | Y | Q | C | L | Q | L | G | A | V | G | 25 |
| B11 | S | D | F | K | F | A | A | Y | I | M | G | W | V | R | Q | A | L | E | W | V | A | I | I | S | H | D | G | I | D | K | Y | Y | T | D | S | V | K | G | R | T | Y | Q | C | L | R | L | G | P | V | G | 26 |
| B12 | S | D | F | L | F | A | A | Y | I | M | G | W | V | R | Q | A | L | E | W | V | A | I | I | S | H | D | G | I | D | K | Y | Y | T | D | S | V | K | G | R | T | Y | Q | C | L | R | L | G | A | V | G | 27 |
| C11 | S | D | F | N | F | A | A | Y | I | M | G | W | V | R | Q | A | L | E | W | V | A | I | I | S | H | D | G | I | D | K | Y | Y | T | D | S | V | K | G | R | T | Y | Q | C | L | Q | L | G | A | V | G | 28 |
| C12 | S | D | F | A | F | A | A | Y | I | M | A | W | V | R | Q | A | L | E | W | V | A | I | I | S | H | D | G | I | D | K | Y | Y | T | D | S | V | K | G | R | T | Y | Q | C | I | R | L | G | A | V | G | 29 |
| D11 | S | D | F | A | F | A | A | Y | I | M | A | W | V | R | Q | A | L | E | W | V | A | I | I | S | H | D | G | I | D | K | Y | Y | T | D | S | V | K | G | R | T | Y | Q | C | I | R | L | G | A | V | G | 30 |
| D12 | S | D | F | H | F | A | A | Y | I | M | A | W | V | R | Q | A | L | E | W | V | A | I | I | S | H | D | G | I | D | K | Y | Y | T | D | S | V | K | G | R | T | Y | Q | C | L | R | L | G | P | V | G | 31 |
| E11 | S | D | F | H | F | A | A | Y | I | M | A | W | V | R | Q | A | L | E | W | V | A | I | I | S | H | D | G | I | D | K | Y | Y | T | D | S | V | K | G | R | T | Y | Q | C | L | R | L | G | A | V | G | 32 |
| E12 | S | D | F | G | F | A | A | Y | I | M | G | W | V | R | Q | A | L | E | W | V | A | I | I | S | H | D | G | I | D | K | Y | Y | T | D | S | V | K | G | R | T | Y | Q | C | L | R | L | G | A | V | G | 33 |
| F11 | S | D | F | D | F | A | A | Y | I | M | A | W | V | R | Q | A | L | E | W | V | A | I | I | S | H | D | G | I | D | K | Y | Y | T | D | S | V | K | G | R | T | Y | Q | C | L | R | L | G | P | V | G | 34 |
| F12 | S | D | F | L | F | A | A | Y | I | M | A | W | V | R | Q | A | L | E | W | V | A | I | I | S | H | D | G | I | D | K | Y | Y | T | D | S | V | K | G | R | T | Y | Q | C | I | R | L | G | A | V | G | 35 |
| G11 | S | D | F | Q | F | A | A | Y | I | M | A | W | V | R | Q | A | L | E | W | V | A | I | I | S | H | D | G | I | D | K | Y | Y | T | D | S | V | K | G | R | T | Y | Q | C | I | R | L | G | A | V | G | 36 |
| G12 | S | D | F | Q | F | A | A | Y | I | M | A | W | V | R | Q | A | L | E | W | V | A | I | I | S | H | D | G | I | D | K | Y | Y | T | D | S | V | K | G | R | T | Y | Q | C | I | R | L | G | P | V | G | 37 |
| H11 | S | D | F | H | F | A | A | Y | I | M | G | W | V | R | Q | A | L | E | W | V | A | I | I | S | H | D | G | I | D | K | Y | Y | T | D | S | V | K | G | R | T | Y | Q | C | L | R | L | G | A | V | G | 38 |
| H12 | S | D | F | H | F | A | A | Y | I | M | A | W | V | R | Q | A | L | E | W | V | A | I | I | S | H | D | G | I | D | K | Y | Y | T | D | S | V | K | G | R | T | Y | Q | C | I | Q | L | G | A | V | G | 39 |

Fig. 2F

SD1 Combi Clone 48 Hour Off Rates

| Clone | 0' Meso | 0' PBS | S/N | 48hr Meso | 48hr PBS | S/N | Fold↓ |
|---|---|---|---|---|---|---|---|
| G7 | 1.80E+06 | 8.60E+04 | 21x | 4.30E+05 | 2.60E+04 | 17x | 4.2x |
| H7 | 1.10E+07 | 9.50E+04 | 116x | 5.80E+06 | 3.60E+04 | 161x | 1.9x |
| D8 | 7.80E+06 | 1.10E+05 | 71x | 2.90E+06 | 3.40E+04 | 85x | 2.7x |
| B11 | 8.60E+06 | 1.00E+05 | 86x | 5.10E+06 | 3.20E+04 | 159x | 1.7x |
| F12 | 1.00E+07 | 1.10E+05 | 91x | 8.90E+06 | 3.70E+04 | 240x | 1.1x |
| G12 | 6.30E+06 | 7.20E+04 | 88x | 3.60E+06 | 5.70E+04 | 63x | 1.8x |

Fig. 2G

SEQUENCE LISTING

```
<160> NUMBER OF SEQ ID NOS: 39

<210> SEQ ID NO 1
<211> LENGTH: 12
<212> TYPE: PRT
<213> ORGANISM: Homo sapiens

<400> SEQUENCE: 1

Gln Ala Ala Phe Glu Lys Thr Ser Ala His Lys Met
1               5                   10


<210> SEQ ID NO 2
<211> LENGTH: 36
<212> TYPE: DNA
<213> ORGANISM: Homo sapiens

<400> SEQUENCE: 2

caagcagcat tcgagaaaac gtcagcccac aagatg                              36


<210> SEQ ID NO 3
<211> LENGTH: 33
<212> TYPE: DNA
<213> ORGANISM: Homo sapiens
<220> FEATURE:
<221> NAME/KEY: misc_feature
<222> LOCATION: (13)..(15)
<223> OTHER INFORMATION: n is a, c, g or t

<400> SEQUENCE: 3

caagcagcat tcnnnaaaac gtcagcccac aag                                 33


<210> SEQ ID NO 4
<211> LENGTH: 33
<212> TYPE: DNA
<213> ORGANISM: Homo sapiens
<220> FEATURE:
<221> NAME/KEY: misc_feature
<222> LOCATION: (16)..(18)
<223> OTHER INFORMATION: n is a, c, g or t

<400> SEQUENCE: 4

caagcagcat tcgagnnnac gtcagcccac aag                                 33


<210> SEQ ID NO 5
<211> LENGTH: 33
<212> TYPE: DNA
<213> ORGANISM: Homo sapiens
```

```
<220> FEATURE:
<221> NAME/KEY: misc_feature
<222> LOCATION: (19)..(21)
<223> OTHER INFORMATION: n is a, c, g or t

<400> SEQUENCE: 5

caagcagcat tcgagaaann ntcagcccac aag                                  33


<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6

tttccggcag tttctacac                                                  19


<210> SEQ ID NO 7
<211> LENGTH: 19
<212> TYPE: DNA
<213> ORGANISM: Artificial Sequence
<220> FEATURE:
<223> OTHER INFORMATION: primer

<400> SEQUENCE: 7

cagcaccttg tcgccttgc                                                  19


<210> SEQ ID NO 8
<211> LENGTH: 50
<212> TYPE: PRT
<213> ORGANISM: Homo sapiens

<400> SEQUENCE: 8

Ser Asp Phe Asp Phe Ala Ala Tyr Glu Met Ser Trp Val Arg Gln Ala
1               5                   10                  15

Leu Glu Trp Val Ala Ile Ile Ser His Asp Gly Ile Asp Lys Tyr Tyr
            20                  25                  30

Thr Asp Ser Val Lys Gly Arg Thr Tyr Tyr Cys Leu Arg Leu Gly Ala
        35                  40                  45

Val Gly
    50


<210> SEQ ID NO 9
<211> LENGTH: 50
<212> TYPE: PRT
<213> ORGANISM: Homo sapiens

<400> SEQUENCE: 9

Ser Asp Phe Asp Phe Ala Ala Tyr Glu Met Ala Trp Val Arg Gln Ala
1               5                   10                  15

Leu Glu Trp Val Ala Ile Ile Ser His Asp Gly Ile Asp Lys Tyr Tyr
            20                  25                  30

Thr Asp Ser Val Lys Gly Arg Thr Tyr Gln Cys Leu Leu Leu Gly Ala
        35                  40                  45

Val Gly
    50


<210> SEQ ID NO 10
<211> LENGTH: 50
<212> TYPE: PRT
<213> ORGANISM: Homo sapiens
```

-continued

```
<400> SEQUENCE: 10

Ser Asp Phe Asp Phe Ala Ala Tyr Glu Met Gly Trp Val Arg Gln Ala
1               5                   10                  15

Leu Glu Trp Val Ala Ile Ile Ser His Asp Gly Ile Asp Lys Tyr Tyr
            20                  25                  30

Asp Asp Ser Val Lys Gly Arg Thr Tyr Gln Cys Leu Arg Leu Gly Ala
        35                  40                  45

Val Gly
    50


<210> SEQ ID NO 11
<211> LENGTH: 50
<212> TYPE: PRT
<213> ORGANISM: Homo sapiens

<400> SEQUENCE: 11

Ser Asp Arg Asp Phe Ala Ala Tyr Glu Met Gly Trp Val Arg Gln Ala
1               5                   10                  15

Leu Glu Trp Val Ala Ile Ile Ser His Asp Gly Ile Asp Lys Tyr Tyr
            20                  25                  30

Asp Asp Ser Val Lys Gly Arg Thr Tyr Gln Cys Leu Arg Leu Gly Ala
        35                  40                  45

Val Gly
    50


<210> SEQ ID NO 12
<211> LENGTH: 50
<212> TYPE: PRT
<213> ORGANISM: Homo sapiens

<400> SEQUENCE: 12

Ser Asp Ser Asp Phe Ala Ala Tyr Glu Met Ala Trp Val Arg Gln Ala
1               5                   10                  15

Leu Glu Trp Val Ala Ile Ile Ser His Asp Gly Ile Asp Lys Tyr Tyr
            20                  25                  30

Thr Asp Ser Val Lys Gly Arg Thr Tyr Gln Cys Leu Arg Leu Gly Ala
        35                  40                  45

Val Gly
    50


<210> SEQ ID NO 13
<211> LENGTH: 50
<212> TYPE: PRT
<213> ORGANISM: Homo sapiens

<400> SEQUENCE: 13

Ser Asp Phe Asp Phe Ala Ala Tyr Glu Met Gly Trp Val Arg Gln Ala
1               5                   10                  15

Leu Glu Trp Val Ala Ile Ile Ser His Asp Gly Ile Asp Lys Tyr Tyr
            20                  25                  30

Asp Asp Ser Val Lys Gly Arg Thr Tyr Gln Cys Leu Arg Leu Gly Ala
        35                  40                  45

Val Gly
    50


<210> SEQ ID NO 14
<211> LENGTH: 50
<212> TYPE: PRT
<213> ORGANISM: Homo sapiens
```

<400> SEQUENCE: 14

Ser Asp Arg Asp Phe Ala Ala Tyr Glu Met Gly Trp Val Arg Gln Ala
1               5                   10                  15

Leu Glu Trp Val Ala Ile Ile Ser His Asp Gly Ile Asp Lys Tyr Tyr
            20                  25                  30

Asp Asp Ser Val Lys Gly Arg Thr Tyr Gln Cys Leu Arg Leu Gly Ala
        35                  40                  45

Val Gly
    50

<210> SEQ ID NO 15
<211> LENGTH: 50
<212> TYPE: PRT
<213> ORGANISM: Homo sapiens

<400> SEQUENCE: 15

Ser Asp Phe Asp Phe Ala Ala Tyr Glu Met Ala Trp Val Arg Gln Ala
1               5                   10                  15

Leu Glu Trp Val Ala Ile Ile Ser His Asp Gly Ile Asp Lys Tyr Tyr
            20                  25                  30

Asp Asp Ser Val Lys Gly Arg Thr Tyr Gln Cys Leu Arg Leu Gly Ala
        35                  40                  45

Val Gly
    50

<210> SEQ ID NO 16
<211> LENGTH: 50
<212> TYPE: PRT
<213> ORGANISM: Homo sapiens

<400> SEQUENCE: 16

Ser Asp Phe Asp Phe Ala Ala Tyr Glu Met Ala Trp Val Arg Gln Ala
1               5                   10                  15

Leu Glu Trp Val Ala Ile Ile Ser His Asp Gly Ile Asp Lys Tyr Tyr
            20                  25                  30

Asp Asp Ser Val Lys Gly Arg Thr Tyr Gln Cys Leu Arg Leu Gly Ala
        35                  40                  45

Val Gly
    50

<210> SEQ ID NO 17
<211> LENGTH: 50
<212> TYPE: PRT
<213> ORGANISM: Homo sapiens

<400> SEQUENCE: 17

Ser Asp Phe Asp Phe Ala Ala Tyr Glu Met Gly Trp Val Arg Gln Ala
1               5                   10                  15

Leu Glu Trp Val Ala Ile Ile Ser His Asp Gly Ile Asp Lys Tyr Tyr
            20                  25                  30

Asp Asp Ser Val Lys Gly Arg Thr Tyr Gln Cys Leu Arg Leu Gly Ala
        35                  40                  45

Val Gly
    50

<210> SEQ ID NO 18
<211> LENGTH: 50
<212> TYPE: PRT
<213> ORGANISM: Homo sapiens -continued

<400> SEQUENCE: 18

```
Ser Asp Gly Asp Phe Ala Ala Tyr Asp Met Ser Trp Val Arg Gln Ala
1               5                   10                  15

Leu Glu Trp Val Ala Ile Ile Ser His Asp Gly Ile Asp Lys Tyr Tyr
            20                  25                  30

Asp Asp Ser Val Lys Gly Arg Thr Tyr Gln Cys Leu Arg Leu Gly Ala
        35                  40                  45

Val Gly
    50
```

<210> SEQ ID NO 19
<211> LENGTH: 50
<212> TYPE: PRT
<213> ORGANISM: Homo sapiens

<400> SEQUENCE: 19

```
Ser Asp Phe Asp Phe Ala Ala Tyr Asp Met Ser Trp Val Arg Gln Ala
1               5                   10                  15

Leu Glu Trp Val Ala Ile Ile Ser His Asp Gly Ile Asp Lys Tyr Tyr
            20                  25                  30

Thr Ser Ser Val Lys Gly Arg Thr Tyr Gln Cys Leu Arg Leu Gly Ala
        35                  40                  45

Val Gly
    50
```

<210> SEQ ID NO 20
<211> LENGTH: 50
<212> TYPE: PRT
<213> ORGANISM: Homo sapiens

<400> SEQUENCE: 20

```
Ser Asp Phe Asp Phe Ala Ala Tyr Ile Met Ser Trp Val Arg Gln Ala
1               5                   10                  15

Leu Glu Trp Val Ala Ile Ile Ser His Asp Gly Ile Asp Lys Tyr Tyr
            20                  25                  30

Ala Asp Ser Val Lys Gly Arg Thr Tyr Gln Cys Leu Arg Leu Gly Ala
        35                  40                  45

Val Gly
    50
```

<210> SEQ ID NO 21
<211> LENGTH: 50
<212> TYPE: PRT
<213> ORGANISM: Homo sapiens

<400> SEQUENCE: 21

```
Ser Asp Phe Asp Phe Ala Ala Tyr Asp Met Ser Trp Val Arg Gln Ala
1               5                   10                  15

Leu Glu Trp Val Ala Ile Ile Ser His Asp Ser Ile Asp Lys Tyr Tyr
            20                  25                  30

Thr Asp Ser Val Lys Gly Arg Thr Tyr Tyr Cys Leu Lys Leu Gly Ala
        35                  40                  45

Val Gly
    50
```

<210> SEQ ID NO 22
<211> LENGTH: 50
<212> TYPE: PRT
<213> ORGANISM: Homo sapiens

<400> SEQUENCE: 22

Ser Asp Phe Asp Phe Ala Ala Tyr Glu Met Ala Trp Val Arg Gln Ala
1 5 10 15

Leu Glu Trp Val Ala Ile Ile Ser His Asp Gly Ile Asp Lys Tyr Tyr
20 25 30

Thr Arg Ser Val Lys Gly Arg Thr Tyr Gln Cys Leu Leu Leu Gly Ala
35 40 45

Val Gly
50

<210> SEQ ID NO 23
<211> LENGTH: 50
<212> TYPE: PRT
<213> ORGANISM: Homo sapiens

<400> SEQUENCE: 23

Ser Asp Phe Asp Phe Ala Ala Tyr Glu Met Gly Trp Val Arg Gln Ala
1 5 10 15

Leu Glu Trp Val Ala Ile Ile Ser His Asp Gly Ile Asp Lys Tyr Tyr
20 25 30

Thr Glu Ser Val Lys Gly Arg Thr Tyr Gln Cys Leu Ser Leu Gly Ala
35 40 45

Val Gly
50

<210> SEQ ID NO 24
<211> LENGTH: 50
<212> TYPE: PRT
<213> ORGANISM: Homo sapiens

<400> SEQUENCE: 24

Ser Asp Phe Thr Phe Ala Ala Tyr Ile Met Gly Trp Val Arg Gln Ala
1 5 10 15

Leu Glu Trp Val Ala Ile Ile Ser His Asp Gly Ile Asp Lys Tyr Tyr
20 25 30

Thr Asp Ser Val Lys Gly Arg Thr Tyr Gln Cys Leu Gln Leu Gly Ala
35 40 45

Val Gly
50

<210> SEQ ID NO 25
<211> LENGTH: 50
<212> TYPE: PRT
<213> ORGANISM: Homo sapiens

<400> SEQUENCE: 25

Ser Asp Phe Glu Phe Ala Ala Tyr Ile Met Ala Trp Val Arg Gln Ala
1 5 10 15

Leu Glu Trp Val Ala Ile Ile Ser His Asp Gly Ile Asp Lys Tyr Tyr
20 25 30

Thr Asp Ser Val Lys Gly Arg Thr Tyr Gln Cys Leu Gln Leu Gly Ala
35 40 45

Val Gly
50

<210> SEQ ID NO 26
<211> LENGTH: 50
<212> TYPE: PRT
<213> ORGANISM: Homo sapiens

```
<400> SEQUENCE: 26

Ser Asp Phe Lys Phe Ala Ala Tyr Ile Met Gly Trp Val Arg Gln Ala
1               5                   10                  15

Leu Glu Trp Val Ala Ile Ile Ser His Asp Gly Ile Asp Lys Tyr Tyr
            20                  25                  30

Thr Asp Ser Val Lys Gly Arg Thr Tyr Gln Cys Leu Arg Leu Gly Pro
        35                  40                  45

Val Gly
    50


<210> SEQ ID NO 27
<211> LENGTH: 50
<212> TYPE: PRT
<213> ORGANISM: Homo sapiens

<400> SEQUENCE: 27

Ser Asp Phe Leu Phe Ala Ala Tyr Ile Met Gly Trp Val Arg Gln Ala
1               5                   10                  15

Leu Glu Trp Val Ala Ile Ile Ser His Asp Gly Ile Asp Lys Tyr Tyr
            20                  25                  30

Thr Asp Ser Val Lys Gly Arg Thr Tyr Gln Cys Leu Arg Leu Gly Ala
        35                  40                  45

Val Gly
    50


<210> SEQ ID NO 28
<211> LENGTH: 50
<212> TYPE: PRT
<213> ORGANISM: Homo sapiens

<400> SEQUENCE: 28

Ser Asp Phe Asn Phe Ala Ala Tyr Ile Met Gly Trp Val Arg Gln Ala
1               5                   10                  15

Leu Glu Trp Val Ala Ile Ile Ser His Asp Gly Ile Asp Lys Tyr Tyr
            20                  25                  30

Thr Asp Ser Val Lys Gly Arg Thr Tyr Gln Cys Leu Gln Leu Gly Ala
        35                  40                  45

Val Gly
    50


<210> SEQ ID NO 29
<211> LENGTH: 50
<212> TYPE: PRT
<213> ORGANISM: Homo sapiens

<400> SEQUENCE: 29

Ser Asp Phe Ala Phe Ala Ala Tyr Ile Met Ala Trp Val Arg Gln Ala
1               5                   10                  15

Leu Glu Trp Val Ala Ile Ile Ser His Asp Gly Ile Asp Lys Tyr Tyr
            20                  25                  30

Thr Asp Ser Val Lys Gly Arg Thr Tyr Gln Cys Ile Arg Leu Gly Ala
        35                  40                  45

Val Gly
    50


<210> SEQ ID NO 30
<211> LENGTH: 50
<212> TYPE: PRT
<213> ORGANISM: Homo sapiens
```

<400> SEQUENCE: 30

Ser Asp Phe Ala Phe Ala Ala Tyr Ile Met Ala Trp Val Arg Gln Ala
1               5                   10                  15

Leu Glu Trp Val Ala Ile Ile Ser His Asp Gly Ile Asp Lys Tyr Tyr
            20                  25                  30

Thr Asp Ser Val Lys Gly Arg Thr Tyr Gln Cys Ile Arg Leu Gly Ala
        35                  40                  45

Val Gly
    50

<210> SEQ ID NO 31
<211> LENGTH: 50
<212> TYPE: PRT
<213> ORGANISM: Homo sapiens

<400> SEQUENCE: 31

Ser Asp Phe His Phe Ala Ala Tyr Ile Met Ala Trp Val Arg Gln Ala
1               5                   10                  15

Leu Glu Trp Val Ala Ile Ile Ser His Asp Gly Ile Asp Lys Tyr Tyr
            20                  25                  30

Thr Asp Ser Val Lys Gly Arg Thr Tyr Gln Cys Leu Arg Leu Gly Pro
        35                  40                  45

Val Gly
    50

<210> SEQ ID NO 32
<211> LENGTH: 50
<212> TYPE: PRT
<213> ORGANISM: Homo sapiens

<400> SEQUENCE: 32

Ser Asp Phe His Phe Ala Ala Tyr Ile Met Ala Trp Val Arg Gln Ala
1               5                   10                  15

Leu Glu Trp Val Ala Ile Ile Ser His Asp Gly Ile Asp Lys Tyr Tyr
            20                  25                  30

Thr Asp Ser Val Lys Gly Arg Thr Tyr Gln Cys Leu Arg Leu Gly Ala
        35                  40                  45

Val Gly
    50

<210> SEQ ID NO 33
<211> LENGTH: 50
<212> TYPE: PRT
<213> ORGANISM: Homo sapiens

<400> SEQUENCE: 33

Ser Asp Phe Gly Phe Ala Ala Tyr Ile Met Gly Trp Val Arg Gln Ala
1               5                   10                  15

Leu Glu Trp Val Ala Ile Ile Ser His Asp Gly Ile Asp Lys Tyr Tyr
            20                  25                  30

Thr Asp Ser Val Lys Gly Arg Thr Tyr Gln Cys Leu Arg Leu Gly Ala
        35                  40                  45

Val Gly
    50

<210> SEQ ID NO 34
<211> LENGTH: 50
<212> TYPE: PRT
<213> ORGANISM: Homo sapiens

<400> SEQUENCE: 34

Ser Asp Phe Asp Phe Ala Ala Tyr Ile Met Ala Trp Val Arg Gln Ala
1 5 10 15

Leu Glu Trp Val Ala Ile Ile Ser His Asp Gly Ile Asp Lys Tyr Tyr
20 25 30

Thr Asp Ser Val Lys Gly Arg Thr Tyr Gln Cys Leu Arg Leu Gly Pro
35 40 45

Val Gly
50

<210> SEQ ID NO 35
<211> LENGTH: 50
<212> TYPE: PRT
<213> ORGANISM: Homo sapiens

<400> SEQUENCE: 35

Ser Asp Phe Leu Phe Ala Ala Tyr Ile Met Ala Trp Val Arg Gln Ala
1 5 10 15

Leu Glu Trp Val Ala Ile Ile Ser His Asp Gly Ile Asp Lys Tyr Tyr
20 25 30

Thr Asp Ser Val Lys Gly Arg Thr Tyr Gln Cys Ile Arg Leu Gly Ala
35 40 45

Val Gly
50

<210> SEQ ID NO 36
<211> LENGTH: 50
<212> TYPE: PRT
<213> ORGANISM: Homo sapiens

<400> SEQUENCE: 36

Ser Asp Phe Gln Phe Ala Ala Tyr Ile Met Ala Trp Val Arg Gln Ala
1 5 10 15

Leu Glu Trp Val Ala Ile Ile Ser His Asp Gly Ile Asp Lys Tyr Tyr
20 25 30

Thr Asp Ser Val Lys Gly Arg Thr Tyr Gln Cys Ile Arg Leu Gly Ala
35 40 45

Val Gly
50

<210> SEQ ID NO 37
<211> LENGTH: 50
<212> TYPE: PRT
<213> ORGANISM: Homo sapiens

<400> SEQUENCE: 37

Ser Asp Phe Gln Phe Ala Ala Tyr Ile Met Ala Trp Val Arg Gln Ala
1 5 10 15

Leu Glu Trp Val Ala Ile Ile Ser His Asp Gly Ile Asp Lys Tyr Tyr
20 25 30

Thr Asp Ser Val Lys Gly Arg Thr Tyr Gln Cys Ile Arg Leu Gly Pro
35 40 45

Val Gly
50

<210> SEQ ID NO 38
<211> LENGTH: 50
<212> TYPE: PRT
<213> ORGANISM: Homo sapiens -continued

```
<400> SEQUENCE: 38

Ser Asp Phe His Phe Ala Ala Tyr Ile Met Gly Trp Val Arg Gln Ala
1               5                   10                  15

Leu Glu Trp Val Ala Ile Ile Ser His Asp Gly Ile Asp Lys Tyr Tyr
            20                  25                  30

Thr Asp Ser Val Lys Gly Arg Thr Tyr Gln Cys Leu Arg Leu Gly Ala
        35                  40                  45

Val Gly
    50


<210> SEQ ID NO 39
<211> LENGTH: 50
<212> TYPE: PRT
<213> ORGANISM: Homo sapiens

<400> SEQUENCE: 39

Ser Asp Phe His Phe Ala Ala Tyr Ile Met Ala Trp Val Arg Gln Ala
1               5                   10                  15

Leu Glu Trp Val Ala Ile Ile Ser His Asp Gly Ile Asp Lys Tyr Tyr
            20                  25                  30

Thr Asp Ser Val Lys Gly Arg Thr Tyr Gln Cys Ile Gln Leu Gly Ala
        35                  40                  45

Val Gly
    50
```

METHOD OF IMPROVING CHARACTERISTICS OF PROTEINS

This is an application filed under 35 USC 1.371(f) based on International Application serial number PCT/US2016/032660 filed 16 May 2016, which claims priority from U.S. provisional application Ser. No. 62/165,173 filed 21 May 2015, Each of the foregoing applications is incorporated herein by reference in its entirety.

BACKGROUND

New generations of therapeutic proteins and antibodies are being engineered and developed that have a host of performance improvements, including modified affinities, increased stability, reduced or increased cross-reactivity, greater solubility, and the like, e.g. Igawa et al, mAbs. 3(3): 243-252 (2011); Bostrom et al, Science, 323: 1610-1614 (2009). An important approach for making such improvements is to create a mutant library from an existing therapeutic protein or therapeutic candidate, then screen library members by various assays until better performing proteins are found. Because such libraries are typically very large, such screening can be expensive and time consuming unless high throughput tools are available. In particular, the target specificity and non-specific binding properties of candidate compounds have been difficult to assess efficiently because of a dearth of high-throughput techniques for this purpose.

In view of the above, endeavors that require an understanding of protein binding reactions, such as protein and antibody engineering, would be advanced by the availability of efficient techniques for creating representative low complexity libraries from which properties of candidate binding compounds could be rapidly assessed/selected.

SUMMARY OF THE INVENTION

Aspects and embodiments of the present invention are exemplified in a number of implementations and applications, some of which are summarized below and throughout the specification.

In one aspect, the invention is directed to methods of improving one or more predetermined characteristics of a protein comprising the steps of: (a) synthesizing a single substitution library for each of a plurality of domains of a protein, each member of a single substitution library having a nucleotide sequence that overlaps a nucleotide sequence of al least one member of a different single substitution library; (b) expressing separately each member of each single substitution library as a pre-candidate protein; (c) selecting members of each single substitution library which encode pre-candidate proteins which exhibit an improvement in the one or more predetermined characteristics to form a selected library for each domain of the protein; (d) shuffling members of the selected libraries in a PCR to produce a combinatorial shuffled library; (e) expressing members of the shuffled library as candidate proteins; and (f) selecting members of the shuffled library which encode candidate proteins whose exhibit an improvement in at least one of the one or more predetermined characteristics. In some embodiments, the plurality of domains covers, or encompasses, a binding site of the protein and the one or more predetermined characteristics are of, or are related to, the binding site, which may be, for example, an antibody binding site, a substrate binding site of an enzyme, or the like.

These above-characterized aspects and embodiments, as well as other aspects and embodiments, of the present invention are exemplified in a number of illustrated implementations and applications, some of which are shown in the figures and characterized in the claims section that follows. However, the above summary is not intended to describe each illustrated embodiment or every implementation of the present invention.

BRIEF DESCRIPTIONS OF THE DRAWINGS

FIGS. 2A-2G show data from application of the invention to generate mutants of single-chain binding compound SD1 which have improved binding affinity to mesothelin.

DETAILED DESCRIPTION OF THE INVENTION

Figure 1:
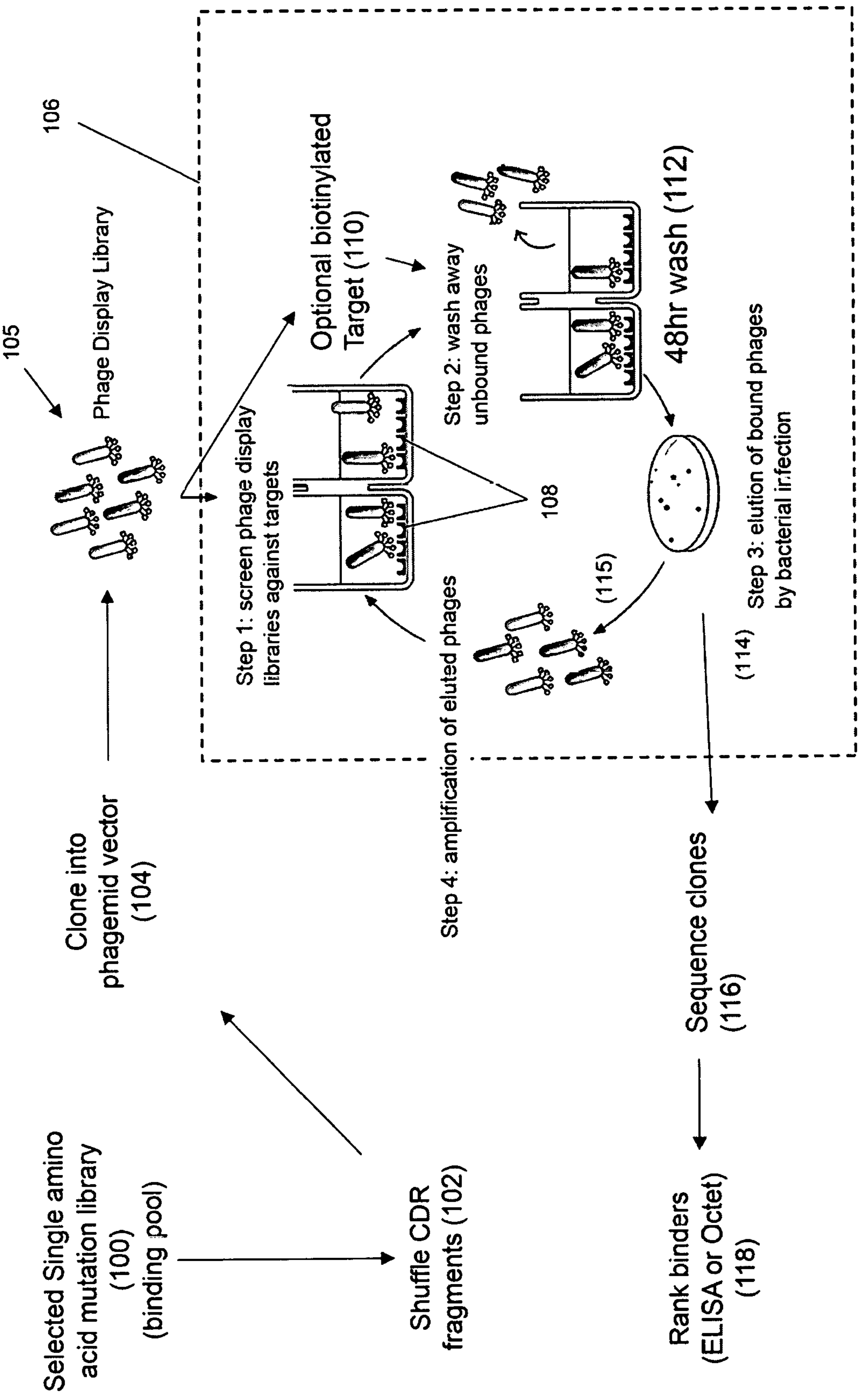
FIG. 1 illustrates a work flow of an exemplary embodiment of the invention.

The practice of the present invention may employ, unless otherwise indicated, conventional techniques and descriptions of organic chemistry, molecular biology (including recombinant techniques), cell biology, and biochemistry, which are within the skill of the art. Such conventional techniques include, but are not limited to, preparation of synthetic polynucleotides, monoclonal antibodies, antibody display systems, nucleic acid sequencing and analysis, and the like. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV); *PCR Primer: A Laboratory Manual; Phage Display: A Laboratory Manual; and Molecular Cloning: A Laboratory Manual* (all from Cold Spring Harbor Laboratory Press); Sidhu, editor, Phage Display in Biotechnology and Drug Discovery (CRC Press, 2005); Lutz, and Bornscheuer, Editors, Protein Engineering Handbook (Wiley-VCH, 2009); Hermanson, Biconjugate Techniques, Second Edition (Academic Press, 2008); and the like.

In one aspect, the invention is directed to methods for improving one or more properties, e.g. affinity, stability, heat tolerance, cross-reactivity, etc., of a protein, which may be a reference binding compound. In some embodiments, a plurality of single-substitution libraries is provided each corresponding to a different domain, or amino acid segment of the protein or reference binding compound such that each member of the single-substitution library encodes only a single amino acid change in its corresponding domain, or amino acid segment. (This allows all of the potential substitutions in a large protein or protein binding site to be probed with a few small libraries.) In some embodiments, the plurality of domains forms or covers a contiguous sequence of amino acids of the protein or reference binding compound. Nucleotide sequences of different single-substitution libraries overlap with the nucleotide sequences of at least one other single-substitution library. In some embodiments, a plurality of single-substitution libraries are designed so that every member overlaps every member of each single-substitution library encoding an adjacent domain. An exemplary single substitution library encoding mutants of a domain of three amino acids (Glu-Lys-Thr, bracketed below) may have the following form:

Reference Protein (SEQ ID NO: 1):

```
...-Gln-Ala-Ala-Phe-[Glu-Lys-Thr]-Ser-Ala-His-Lys-
Met-...
```

Reference Protein Nucleic Acid Sequence (SEQ ID NO: 2):

```
...-CAA-GCA-GCA-TTC-[GAG-AAA-ACG]-TCA-GCC-CAC-AAG-
ATG-...
```

Members of a single-substitution library for the Glu-Lys-Thr domain with 12-nucleotide overlaps (SEQ ID NO: 3, SEQ ID NO: 4, SEQ ID NO: 5):

```
CAA-GCA-GCA-TTC-[NNN-AAA-ACG]-TCA-GCC-CAC-AAG

CAA-GCA-GCA-TTC-[GAG-NNN-ACG]-TCA-GCC-CAC-AAG

CAA-GCA-GCA-TTC-[GAG-AAA-NNN]-TCA-GCC-CAC-AAG
```

where "NNN" is a "wildcard" codon as described below.

Proteins, e.g. binding compound, expressed from such single-substitution libraries are separately selected to obtain a subset of variants in each library which has properties (or one or more characteristics) at least as good as, those of the reference protein or reference binding compound and whose resultant library is reduced in size. (That is, the number of nucleic acids encoding the selected set of binding compounds is smaller than the number of nucleic acids encoding members of the original single-substitution library). Such properties (or characteristics) include, but are not limited to, affinity to a target compound, stability with respect to various conditions such as heat, high or low pH, enzymatic degradation, cross-reactivity to other proteins and the like. The selected compounds from each single-substitution library are referred to herein interchangeably as "pre-candidate compounds," or "pre-candidate proteins." In regard to a property or characteristic of a protein, "at least as good as" means that whenever a property or characteristic of a protein may be represented by a value (for example, a temperature or a pH (or the like) at which an activity changes (e.g. drops) a predetermined amount, an affinity to a target compound, or the like), the value of such property or characteristic of a pre-candidate protein is greater than or less than the corresponding value of the reference protein. Depending on the property or characteristic under consideration, in some implementations of the method, pre-candidate proteins having values larger than that of the reference protein are selected, and in other embodiments, pre-candidate proteins having values less than that of the reference protein are selected.

Nucleic acid sequences encoding the pre-candidate compounds from the separate single-substitution libraries are then shuffled in a PCR to generate a shuffled library, e.g. Stemmer, U.S. Pat. Nos. 6,444,468; 6,132,970; 5,830,721; Stemmer, Proc. Natl. Acad. Sci., 91: 10747-10751 (1994); Wu et al, U.S. patent publication 2006/0228350; all of the foregoing references being incorporated herein by reference for their teachings on PCR-based gene shuffling. That is, the term "shuffling" in reference to separate single-substitution libraries means that such libraries are combined in a PCR mixture and a PCR is carried out so that members of the separate single-substitution libraries are linked in the resulting PCR product. As noted above, it is desirable that sequences of at least a pair of single-substitution libraries overlap so that strands of members of different single-substitution libraries can anneal to one another and be extended in the PCR. In other words, it is desirable that sequences of at least a pair of single-substitution libraries can anneal to one another and function as primers and templates to one another in the PCR. In some embodiments, it is desirable that every single-substitution library of a plurality have members whose sequences overlap those of an adjacent single-substitution library. The amount or degree of overlap may vary widely. In some embodiments, the degree of overlap is the same as the length of a typical primer sequence, e.g. as described in the definition section. In other embodiments, the degree of overlap may vary from 6 to 100 nucleotides, or from 6 to 40 nucleotides.

FIG. 1 provides a schematic of a work flow of one embodiment of the invention. Libraries of pre-candidate compounds are generated from single substitution libraries and selected for binding to the target protein(s) (100), after which the pre-candidate libraries are shuffled (102) to produce a combinatorial library of nucleic acids encoding candidate compounds which, in turn, are cloned (104) into a convenient expression vector, such as a phagemid expression system. Phage (105) expressing candidate compounds then undergo one or more rounds of selection (106) for improvements in desired properties, such as binding affinity to a target molecule (108). Target molecules may be adsorbed or otherwise attached to a surface of a well or other reaction container as illustrated in FIG. 1, or target molecules may be derivatized with a binding moiety, such as biotin (110), which after incubation with candidate binding compounds may be captured with a complementary moiety, such as streptavidin, bound to beads, such as magnetic beads, for washing. In one particular selection regimen of interest, candidate binding compounds undergo a prolonged wash step (112) so that only candidate compounds with very low dissociation rates from a target molecule are selected. Exemplary wash times for such embodiments are at least 8 hours; or in other embodiments, at least 24 hours; or in other embodiments, at least 48 hours; or in other embodiments, at least 72 hours. In other embodiments, the duration of a washing step may be determined by the fraction of candidate binding compounds remaining bound to target. That is, bound compounds may be subjected to wash conditions for as long (or as many depending on the implementation) as it takes until 50 percent of the binding compounds remain bound, or until 10 percent of the binding compounds remain bound, or until 1 percent of the binding compounds remain bound. Alternatively, wash durations (or number depending on implementation) may be determined in reference to fraction of binding compound eluted from target. Isolated clones after selection may be amplified and subjected to additional cycles of selection (115) or they may be analyzed (114), for example by sequencing (116) and by making comparative measurements of binding affinity, for example, by ELISA, surface plasmon resonance binding, bio-layer interferometry (e.g. Octet system, ForteBio, Menlo Park, Calif.) or the like (118).

Selection for Improved Physical, Chemical and Biological Characteristics

In some embodiments, the method of the invention may be used to obtain a binding compound with equivalent or better affinity as that of a reference binding compound, but which has superior stability with respect to selected destabilizing agents. In some embodiments, the process described above can also be run with members of the single substitution libraries having first been treated with a destabilizing agent (heat, low pH, proteases, or the like). In other words, its members form "stressed" libraries. The pre-candidate binding compounds from such libraries that lose binding affinity after being "stressed" contain destabilizing residues. A goal is to identify mutants that bind the antigen at least as well or better than wild type in the "stressed" library. It is expected that several stabilizing mutations could be combined to dramatically increase the stability of the resultant molecule, for example, by shuffling to create a second-stage combinatorial library from such mutants and conducting a second round of stressing followed by a binding selection. In some embodiments, the above may be implemented in accordance with the invention to increase stability of a selected nucleic acid-encoded binding compound (i.e. reference binding compound) without loss of affinity for a ligand by the steps of: (a) treating a library (or libraries) of pre-candidate binding compounds with a destabilizing agent to form a treated/stressed library or libraries of pre-candidate binding compounds, each pre-candidate binding compound being comprised of or encoded by a nucleotide sequence; (b) reacting under binding conditions one or more ligands with the treated library or libraries of pre-candidate binding compounds (c) shuffling the selected clones from one or more of the libraries, (d) subjecting the shuffled library to a similar stress and (e) selecting at least one candidate binding compound from a subset of candidate binding compounds whose affinity is equal to or greater than that of the selected nucleic acid-encoded binding compound (that is, the reference binding compound), thereby providing a nucleic acid-encoded binding compound with increased stability with respect to the reference binding compound without loss of affinity.

In some embodiments, for example, for binding compounds expressed in phage display systems, exemplary conditions for stressing a subset include (i) exposing phage to elevated temperatures, e.g. in the range of 40-70° C. for a period of time, e.g. in the range of 5-60 minutes; (ii) exposing phage to low pH or high pH, e.g. pH in the range of 1-4 or 9-13, for a period of time, e.g. in the range of 5-60 minutes; (iii) exposing phage to various proteases tat various activities over a range for a period of time, e.g. 15-30 minutes, or 1-4 hours, or 1 hour to 24 hours, depending on the protease and specific activity. Exemplary proteases for stability testing include, but are not limited to, serum proteases: trypsin, chymotrypsin; cathepsins, including but not limited to cathepsin A and cathepsin endopeptidases, such as, matrix metalloproteinases (MMPs) including, but not limited to, MMP-1, MMP-2, MMP-9; or the like.

In some embodiments, the method of the invention may be used to obtain a binding compound with equivalent or better affinity to a target antigen or molecule as that of a reference binding compound, but that has reduced cross reactivity, or in some embodiments, increased cross reactivity, with selected substances, such as ligands, proteins, antigens, or the like, other than the substance or epitope for which a reference binding compound is specific, or is designed to be specific for. In regard to the latter, a candidate therapeutic antibody may be more successfully tested in animal models if the antibody reacted with both its human target and the corresponding target of the animal model, e.g. mouse or monkey. Thus, in some embodiments, the method of the invention may be employed to increase cross reactivity with one or more selected substances or compounds from a first set, such as corresponding animal model targets or other protein family members. In other embodiments, the method of the invention is employed to reduce cross reactivity of a binding compound, such as a candidate therapeutic antibody, for example, to reduce potential side effects in a patient. As above, a subset of candidate compounds is identified based on affinity (i.e. having equivalent or higher affinity than that of the reference compound). Candidate compounds from the subset may then be combined with one or more substances or compounds of a second set (other than the target antigen in one or more binding reactions (e.g. each at different phage concentrations)) and selected for candidate binding compounds which are not depleted by such substances. The choice of substances may vary widely, and may include tissues, cell lines, selected proteins, tissue arrays, protein microarrays, or other multiplex displays of potentially cross reactive compounds. Guidance for selecting such antibody cross reaction assays may be found in the following exemplary references: Michaud et al. Nature Biotechnology, 21(12): 1509-1512 (2003); Kijanka et. al, J. Immunol. Methods, 340(2): 132-137 (2009); Predki et al, Human Antibodies, 14(1-2): 7-15 (2005); Invitrogen Application Note on Protoarray™ Protein Microarray (2005); and the like. In such binding reactions, nucleic acids encoding binders and non-binders from the subset are determined in accordance with the invention, thereby providing significant enrichment or depletion of each candidate binding compound of the subset for the one or more selected substances for which cross reactivity modulation was sought. As above, depletion of cross reactive mutants may be used to generate a second stage library to identify binding compounds with further reduced cross reactivity with the selected substances.

In some embodiments, the above may be implemented in accordance with the invention to identify one or more binding compounds with increased cross reactivity with or to a selected set of substances or compounds compared to that of a reference binding compound without loss of affinity for the original ligand. Such method may be carried out by the steps of: (a) synthesizing, a single substitution library for each of a plurality of domains of a protein binding site, each member of a single substitution library having a nucleotide sequence that overlaps a nucleotide sequence of at least one member of a different single substitution library; (b) expressing separately each member of each single substitution library as a pre-candidate protein; (c) selecting members of each single substitution library which encode pre-candidate proteins which bind to a binding partner that differs from the original binding target [e.g. a desired cross-reaction target(s)], (d) shuffling members of the selected libraries in a PCR to produce a combinatorial shuffled library; (e) expressing members of the shuffled library as candidate proteins; and (f) selecting members of the shuffled library one or more times for candidate proteins which bind the original binding partner and (g) further selecting the candidate proteins for binding to the desired cross-reactive target(s) thereby providing a nucleic acid-encoded binding compound(s) with increased cross reactivity for the one or more substances with respect to the reference binding compound without loss of affinity for the original ligand. Likewise, a method may be implemented for obtaining a binding compound with decreased reactivity to a selected cross-reactive substance(s) or compound(s) or epitope(s) by substituting step (g) with the following step: depleting candidate binding compounds one or more times from the subset of candidate binding compounds which bind to the undesired cross-reactive compound.

Protein Display Systems

Features of any peptide or protein display system are: 1. Tight linkage between the expressed proteins and their encoding nucleic acid; and 2. Expression of the protein in a format that allows it to be assayed and separated based on some biochemical activity (for example, binding strength, susceptibility to enzymatic action, or the like). For the purposes of this discussion, protein display systems can be separated into two groups based on the number of displayed proteins per display unit, either polyvalent or monovalent. The polyvalent display systems such as yeast display (references 1 and 2 below), mammalian display systems (references 3 and 4 below) and bacterial display systems (reference 5) express the gene(s) of interest (often diverse antibody libraries) as proteins tethered to the cell surface by means of a membrane anchor, similar to a native surface immunoglobulin found on the plasma membrane of normal B-cells. DNA encoding the library clones is transformed into the cell type of interest such that each cell receives at most one clone from the library. The resultant population of cells will each express tens to tens of thousands of copies of a single protein clone on their cell surfaces. This population of cells can then be exposed to limiting amounts of fluorescently labeled target antigen and die best binding clones will bind the most antigen and they can be identified and isolated using a fluorescence-activated cell sorter (FACS). Unfortunately accurate quantitation in polyvalent display systems is complicated by cooperative binding effects (avidity) between the multiple copies of the displayed molecule on the same cell (reference 6). This problem is especially pronounced if the antigen is polyvalent (TNF, IgG) or bound to a cell surface (e.g. CD 20, CD3, GPCRs, ion channels, and the like).

Many of the viral and phage-based protein display systems are also polyvalent in nature, but the display units are too small to detect on the FACS, so accurate quantitation is even more difficult. These systems also suffer from avidity problems if multiple binding compounds are expressed simultaneously on the same phage/viral particle. Under such conditions it is difficult to determine whether an observed binding strength is due to the combined effect of two expressed binding compounds versus the effect of a single very high affinity binding compound. Such avidity problems may be minimized by regulating the expression of candidate binding compound in a host using conventional techniques. In one embodiment in which a phage display system expresses Fab fragments, e.g. as disclosed in FIG. 5, regulation of Fab expression is adjusted so that the fraction of phage expressing a Fab is in the range of from about 0.002 to 0.001, or in the range of about 0.001 to 0.0005.

The monovalent phage (reference 7) and viral (reference 8) systems, along with the ribosome display systems (references 9 and 10) express an average of ≤1 molecule of the displayed molecule per display unit. These systems yield accurate measurements of the true affinity of the binding site in question for each clone in the library. Generally these systems are used to display large, diverse libraries of binding elements. Small subpopulations of clones are then selected from these libraries based on their increased ability to bind the target antigen relative to other members of the library. After selection (often multiple rounds of selection) the resultant clones are isolated and characterized (e.g. as disclosed in U.S. Pat. No. 7,662,557 which is incorporated herein by reference). This is a good strategy for isolating initial binders to a given target antigen from a very large and diverse library, but is not an efficient method for comprehensively scanning a single protein binding site for the purposes of protein engineering. To achieve this goal one would like to characterize the effect of every possible engineering change and then design and construct an optimized binding site based on: affinity, stability, cross-reactivity, manufacturing yield, etc. Therefore it would be desirable to analyze the binding strength of every member of a saturated, single substitution library/group of libraries of the binding site in question. The above protein display techniques are disclosed in the following exemplary references, which are incorporated herein by reference: (1) Wittrup, K D; Current Opinion in Biotechnology 12: 395-399 (2001) (Protein engineering by cell-surface display); (2) Lauren R. Pepper, Yong Ku Cho, Eric T. Boder and Eric V. Shusta; Combinatorial Chemistry & High Throughput Screening 11: 127-134 (2008); (3) Yoshiko Akamatsu, Kanokwan Pakabunto, Zhenghai Xu, Yin Zhang, Naoya Tsurushita; Journal of Immunological Methods 327: 40-52 (2007); (4) Chen Zhou, Frederick W. Jacobsen, Ling Cai, Qing Chen and Weyen David Shen; mAbs 2(5): 1-11 (2010); (5) Patrick S Daugherty; Current Opinion in Structural Biology 17:474-480 (2007) (Protein engineering with bacterial display); (6) Clackson and Lowman (editors), Phage Display (2009); (7) Hennie R Hoogenboom, Andrew D Griffiths, Kevin S Johnson, David J Chiswell, Peter Hudson and Greg Winter; Nucleic Acids Research 19(15): 4133-4137 (1991); (8) Francesca Gennari, Luciene Lopes, Els Verhoeyen, Wayne Marasco, Mary K. Collins; Human Gene Therapy 20: 554-562 (2009); (9) Christiane Schaffitzel, Jozef Hanes, Lutz Jermutus, Andreas Pluckthun; Journal of Immunological Methods 231: 119-135 (1999) (ribosome display); (10) Robert A Irving, Gregory Coia, Anthony Roberts, Stewart D Nuttall, Peter J Hudson; Journal of Immunological Methods 248: 31-45 (2001) (ribosome display); (11) Arvind Rajpal, Nurten Beyaz, Lauric Haber, Guido Cappuccilli, Helena Yee, Ramesh R Bhatt, Toshihiko Takeuchi, Richard A Lerner, Roberto Crea; PNAS 102 (24): 8466-71(2005). Some of the above techniques are also disclosed in the following patents, which are incorporated herein by reference: U.S. Pat. Nos. 7,662,557; 7,635,666; 7,195,866; 7,063,943; 6,916,605; and the like.

Further protein display systems for use with the invention include baculoviral display systems, adenoviral display systems, lentivirus display systems, retroviral display systems, SplitCore display systems, as disclosed in the following references: Sakihama et al, PLosOne 3(12): e4024 (2008); Makela et al, Combinatorial Chemistry & High Throughput Screening, 11: 86-98 (2008); Urano et al. Biochem. Biophys. Res Comm., 308: 191-196 (2003); Gennari et al. Human Gene Therapy, 20: 554-562 (2009); Taube et al, PLosOne, 3(9) e3181 (2008); Lim et al, Combinatorial Chemistry & High Throughput Screening, 11:111-117(2008); Urban et al, Chemical Biology, 6(1): 61-74 (2011); Buchholz et al, Combinatorial Chemistry & High Throughput Screening, 1: 99-110 (2008); Walker et al, Scientific Reports, 1(5): (14 Jun. 2011); and the like.

In some embodiments, the invention employs conventional phage display systems for improving one or more properties of an antibody/protein binding compound, particularly a preexisting antibody/protein binding compound. Unlike prior applications of display technologies, which employ repeated cycles of selection, washing, elution and amplification, to identify individual phage from a large combinatorial library, e.g. $>10^8$-$10^9$ clones, in the present invention, multiple small and focused libraries, e.g. $10^3$-$10^4$ clones each, or in some embodiments $10^4$-$10^5$ clones each are selected in one or more serial binding reactions, poorly binding clones are eliminated thus reducing the size of each library. From such analysis, subsets are selected and shuffled, the resultant combinatorial shuffled library is further selected based on other properties of interest, such as, affinity, stability, cross-reactivity, and the like. Factors affecting such binding reactions are well-known in the art and include: the number of phage to include in the reaction, the stringency of the reaction mixture; the number of target molecules to include in the reaction; presence or absence of blocking agents, such as, bovine serum albumin, gelatin, casein, or the like, to reduce nonspecific binding; the length and stringency of a wash step to deplete poor binders and enrich good binders; the nature of an elution step to remove binders from the target molecules; the format of target molecules used in the reaction, which, for example, may be bound to a solid support or derivatized with a capture agent, e.g. biotin, and may be free in solution; the phage protein into which candidate binding compounds are inserted; and the like. In some embodiments, target molecules, such as proteins, are purified and directly immobilized on a solid support such as a bead or microtiter plate. This enables the physical separation of bound and unbound phage simply by washing the support. Numerous supports are available for this purpose, including modified affinity resins, glass beads, modified magnetic beads, plastic supports, and the like. Useful supports are those that have low background for nonspecific phage binding and that present the target molecules in a native configuration and at a desirable concentration.

In some embodiments, a nucleic acid-encoded binding, compound is an antibody fragment expressed by a phage. In one embodiment, such phage is a filamentous bacteriophage and the antibody fragment is expressed as part of a coat protein. In particular, such phage may be a member of the Ff class of bacteriophages. In a further embodiment, the host of such filamentous bacteriophage is *E. coli*. In another embodiment, a phagemid-helper phage system is used for displaying antibody fragments. Phagemids may be maintained as plasmids in a host bacteria and phage production induced by further infection with a helper phage. Exemplary phagemids include pComb3 and its related family members e.g. disclosed in Barbas et al, Proc. Natl. Acad. Sci., 88: 7978-7982 (1991), and pHEN1 and its related family members, e.g. disclosed in Hoogenboom et al, Nucleic Acids Research, 19: 4133-4137 (1991); and U.S. Pat. Nos. 5,969,108; 6,806,079; 7,662,557; and related patents, which are incorporated herein by reference. In a particular embodiment, an antibody fragment is expressed as a fusion protein with phage coat protein g3p.

Libraries of Nucleic Acid-Encoded Binding Compounds

As mentioned above, a feature of the invention is the use of focused single substitution libraries in which large binding domains can be scanned to completion using a small number (3-30) of sub-domain libraries. In some embodiments this limits the need for successive cycles of selection, elution, and amplification and for the use of multiple large, combinatorial libraries, as required in conventional approaches. The size of such focused libraries of candidate binding compounds is influenced by at least two factors: the size of the sub-domains that are chosen to span the protein domain and the difficulty of synthesizing polynucleotides that encode library members. That is, the larger the protein domain to be scanned, the larger the number and or the size of the sub-domain libraries. Likewise, a larger library of candidate compounds means a greater number of polynucleotides need to be synthesized. Thus, particular applications may involve conventional design choices between scale of implementation and cost. In some embodiments, focused libraries are obtained by varying amino acids in a limited number of locations one or two at a time within a pre-existing binding compound, which may be the same as, or equivalent to, a reference binding compound. Preferably amino acids are varied at different positions one at a time. Thus, for example, members of a library of candidate binding compounds may have nucleotide sequences identical to that encoding the pre-existing binding compound except for a single codon position. At that position, most library members will have a codon different from that of the pre-existing binding compound.

Such libraries may include members having an amino acid insertion or deletion at such location and may not necessarily include members with every possible codon at such location. Libraries may contain members corresponding to such substitutions (and insertions or deletions) at each of a set of amino acid locations within the pre-existing binding compound. The locations may be contiguous or non-contiguous. In some embodiments, the number of locations where codons are varied are in the range of from 1 to 500; in some embodiments, the number of such locations are in the range of from 1 to 250; in other embodiments, the number of such locations are in the range of from 10 to 100; and in still other embodiments, the number of such locations are in the range of from 10 to 250. A pre-existing binding compound may be any pre-existing antibody or binding protein for which sequence information is available (or can be obtained). Typically, a pre-existing binding compound is a commercially important binding compound, such as an antibody drug or drug candidate, for which one desires to modify one or more properties, such as affinity, alteration of cross reactivity, increase in stability, aggregation resistance, or the like, as discussed above. In one embodiment, the locations where codons are varied comprise the $V_H$ and $V_L$ regions of an antibody, including both codons in framework regions and in CDRs; in another embodiment, the locations where codons are varied comprise the CDRs of the heavy and light chains of an antibody, or a subset of such CDRs, such as solely CDR1, solely CDR2, solely CDR3, or pairs thereof.

In another embodiment, locations where codons are varied occur solely in framework regions; for example, a library of the invention may comprise single codon changes solely from a reference binding compound solely in framework regions of both $V_H$ and $V_L$ numbering in the range of from 10 to 250. In another embodiment, the locations where codons are varied comprise the CDR3s of the heavy and light chains of the antibody, or a subset of such CDR3s. In another embodiment, the number of locations where codons of $V_H$ and $V_L$ encoding regions are varied are in the range of from 10 to 250, such that up to 100 locations are in framework regions. In another embodiment, nucleic acid encoded binding compounds are derived from a pre-existing binding compound, such as a pre-existing antibody or other binding protein. Exemplary pre-existing binding compounds include, but are not limited to, antibody-targeted drugs or antibody-based drugs such as adalimumab (Humira), bevacizumab (Avastin), cetuximab (Erbitux), efalizumab (Raptiva), infliximab (Remicade), panitumumab (Vectubix), ranibuzumab (Lucentis), rituximab (Rituxan), trastuzumab (Herceptin), and the like, growth factors or growth factor receptors, ligands and signaling receptors, hormones and hormone receptors, clotting factors and clotting factor receptors, enzymes, matrix proteins and matrix binding receptors, cytokines and cytokine receptors, etc.

In some embodiments, the above codon substitutions are generated by synthesizing coding segments with degenerate codons. The coding segments are then litigated into a vector, such as a replicative form of a phage or phagemid, to form a library. Many different degenerate codons may be used with the present invention, such as those shown in Table I.

TABLE I

Exemplary Degenerate Codons

| Codon* | Description | Stop Codons | Number |
|---|---|---|---|
| NNN | All 20 amino acids | TAA, TAG, TGA | 64 |
| NNK or NNS | All 20 amino acids | TAG | 32 |
| NNC | 15 amino acids | none | 16 |
| NWW | Charged, hydrophobic | TAA | 16 |
| RVK | Charged, hydrophilic | none | 12 |
| DVT | Hydrophilic | none | 9 |
| NVT | Charged, hydrophilic | none | 12 |
| NNT | Mixed | none | 16 |
| VVC | Hydrophilic | none | 9 |
| NTT | Hydrophobic | none | 4 |
| RST | Small side chains | none | 4 |
| TDK | Hydrophobic | TAG | 6 |

*Symbols follow the IUB code: N = G/A/T/C, K = G/T, S = G/C, W = A/T, R = A/G, V = G/A/C, and D = G/A/T.

In some embodiments, the size of binding compound libraries used in the invention varies from about 1000 members to about $1\times10^5$ members; in some embodiments, the size of libraries used in the invention varies from about 1000 members to about $5\times10^4$ members; and in further embodiments, the size of libraries used in the invention varies from about 2000 members to about $2.5\times10^4$ members. Thus, nucleic acid libraries encoding such binding compound libraries would have sizes in ranges with upper and lower bounds up to 64 times the numbers recited above.

EXAMPLE

Obtaining Optimized Anti-Mesothelin sdFv Antibodies with Improved Binding Affinity 43 phagemid library inserts were synthesized containing DNA sequences encoding the sdFv shown in FIG. 2A. Each insert had the codon for one of the amino acids (underlined) replaced with the degenerate codon, NNN. These inserts were cloned into the phagemid to produce 43 mini-libraries which each encoded 19 variant sdFvs and I wild type. These minilibraries were transformed into the *E. coli* strain SS320 and the transformants were mixed into three sub-libraries encompassing CDR1, CDR2 and CDR3 of the sdFv. These sub-libraries were grown up and infected with the M13K07 helper phage and three phage libraries were produced.

A maxisorp plate was coated with 100 ng/well mesothelin-Fc in three wells and incubated at 4° C. overnight. The next morning the coat antigen solution was removed and the wells were blocked with 350 ul of Blocking Buffer (PBS+ 3% BSA) for 90' at room temperature. The Blocking Buffer was removed and $5\times10^{10}$ phage (diluted in Wash Buffer—PBS+0.5% BSA+0.05% Tween20) from each library was added to a well on the plate. These binding reactions were incubated at room temperature for 75'. The phage dilutions were then removed and the wells were washed with 350 ul Wash Buffer five times. 200 ul Wash buffer was added to the wells and they were allowed to wash for an additional 3 hours. Following this extended wash phage from each of the wells were eluted with 100 mM glycine (pH2.2) at room temperature for 15' and then recovered and the pH was neutralized with 3 ul 2M Tris Base.

Figure 2B:
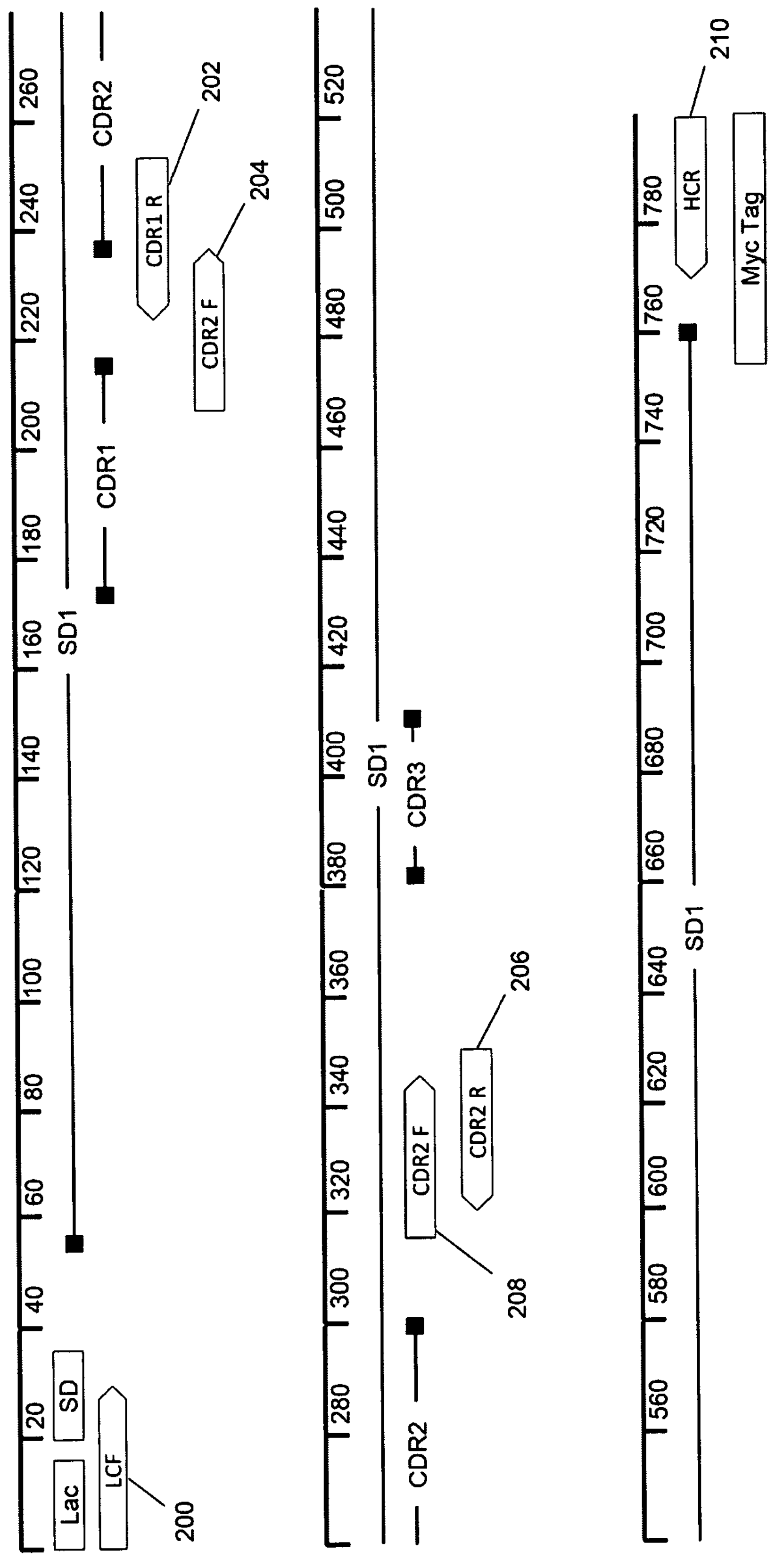

A map of the remainder of the process is shown in FIG. 2B. Briefly the relevant portion of each selected single substitution library was isolated via PCR using primers LCF (200) and 135 (202) for the CDR1 library; 136 (204) and 137 (206) for the CDR2 library; and 138 (208) and 121 (210) for the CDR3 library FIG. 2B. The three library PCR products were then gel purified and the fragments were mixed in a 1:1:1 molar ratio and stitched together through their overlapping homologies in an assembly PCR reaction. The assembled combinatorial products were then amplified using primers LCF (200) and 121 (210). This combinatorial library fragment was then used to make two phagemid libraries: the first via direct cloning of the amplified library into the phagemid vector (CDR library) and the second via an additional DNase1 shuffling reaction (Stemmer, Nature 370: 389-91 1994) and then cloning into the phagemid vector (DNase library). Phage were produced from the two libraries and 3 rounds of increasingly stringent binding reactions were run. In this case the first round binding reaction used a 4 hour wash step. The bound phage were recovered using an acid elution from the well and were then infected into SS320 cells and amplified with the M13FC07 helper phage. The second round binding reaction was run using an 18 hour wash step with the wild type clone included as a control to monitor the efficiency of the wash step and PBS coated wells included to measure non-specific binding of the phage to the wells FIG. 2C. The number of rescued phage from each sample was determined using a SyberGreen qPCR amplification reaction to detect the single stranded phagemid DNA with the primers CmF2 (5' TTTCCGGCAGTTTCTACAC 3') (SEQ ID NO: 6) and CmR1 (5' CAGCACCTTGTCGCCTTGC3') (SEQ ID NO: 7) on a Applied Biosystems StepOnePlus Real-time PCR system using a standard curve with phage diluted in PBS at $3\times10^8$, $3\times10^7$, $3\times10^6$, $3\times10^5$, $3\times10^4$ and 0 phage/well. The rescued phage from the 18 hr reactions were again amplified and a third round of binding reactions were run in a similar fashion using a 48 hr wash step FIG. 2D. Following this final round of binding the rescued phage were used to infect SS320 cells and individual transductants were selected for sequencing FIGS. 2E and 2E.

Phage were produced from 3 clones derived from each library after the third round of selection (D08, G07, H07 (SEQ ID NO: 15, SEQ ID NO: 20, SEQ ID NO: 22, respectively) from the CDR shuffled library (FIG. 2E) and B11, F12 and G12 (SEQ ID NO: 26, SEQ ID NO: 35, SEQ ID NO: 37, respectively) from the DNase shuffled library (FIG. 2F)). These phage clones were tested in binding reactions with a 48 hr wash step and each clone showed a slower off rate (tighter binding) than the parental clone FIG. 2G.

While the present invention has been described with reference to several particular example embodiments, those skilled in the art will recognize that many changes may be made thereto without departing from the spirit and scope of the present invention. The present invention is applicable to a variety of sensor implementations and other subject matter, in addition to those discussed above.

Definitions

Unless otherwise specifically defined herein, terms and symbols of nucleic acid chemistry, biochemistry, genetics, and molecular biology used herein follow those of standard treatises and texts in the field, e.g. Kornberg and Baker, DNA Replication, Second Edition (W. H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Abbas et al, Cellular and Molecular Immunology, 6th edition (Saunders, 2007).

"Antibody" or "Immunoglobulin" means a protein, either natural or synthetically produced by recombinant or chemical means, that is capable of specifically binding to a particular antigen or antigenic determinant, which may be a target molecule as the term is used herein. Antibodies, e.g. IgG antibodies, are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intra-chain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Typically the binding characteristics, e.g. specificity, affinity, and the like, of an antibody, or a binding compound derived from an antibody, are determined by amino acid residues in the $V_H$ and $V_L$ regions, and especially in the CDR regions. The constant domains are not involved directly in binding an antibody to an antigen. Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., $IgG_1$, $IgG_2$, $IgG_3$, $IgG_4$, $IgA_1$, and $IgA_2$. "Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, $F(ab')_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multi specific or multivalent structures formed from antibody fragments. The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each mAb is directed against a single determinant on the antigen. In addition to their specificity, the monoclonal antibodies are advantageous in that they can be synthesized by hybridoma culture or by bacterial, yeast or mammalian expression systems, uncontaminated by other immunoglobulins.

"Binding compound" means a compound that is capable of specifically binding to a particular target molecule or group of target molecules. Examples of binding compounds include antibodies, receptors, ligands, hormones, clotting factors, binding proteins, transcription factors, signaling molecules, viral proteins, lectins, nucleic acids, aptamers, and the like, e.g. Sharon and Lis, Lectins, 2nd Edition (Springer, 2006); Klussmann, The Aptamer Handbook: Functional Oligonucleotides and Their Applications (John Wiley & Sons, New York, 2006). As used herein, "antibody-based binding compound" means a binding compound derived from an antibody, such as an antibody fragment, including but not limited to, Fab, Fab', $F(ab')_2$, and Fv fragments, or recombinant forms thereof, such as bispecific constructs. In some embodiments, an antibody-based binding compound comprises a scaffold or framework region or an antibody and CDR regions of an antibody.

"Complementary-determining region" or "CDR" means a short sequence (usually up to 13 to 25 amino acids) in the variable domains of immunoglobulins. The CDRs (six of which are present in IgG molecules) are the most variable part of immunoglobulins and contribute to their diversity by making specific contacts with a specific antigen, allowing in to recognize a vast repertoire of antigens with a high affinity, e.g. Beck et al, Nature Reviews Immunology, 10: 345-352 (2010). Several numbering schemes, such as the Kabat numbering scheme, provide conventions for describing amino acid locations of CDRs within variable regions of immunoglobulins.

"Complex" as used herein means an assemblage or aggregate of molecules in direct or indirect contact with one another. In some embodiments, "contact," or more particularly, "direct contact" in reference to a complex of molecules, or in reference to specificity or specific binding, means two or more molecules are close enough so that attractive noncovalent interactions, such as Van der Waal forces, hydrogen bonding, ionic and hydrophobic interactions, and the like, dominate the interaction of the molecules. In such embodiments, a complex of molecules is stable in that under assay conditions, the presence of the complex is thermodynamically favorable. As used herein, "complex" may refer to a stable aggregate of two or more proteins, which is equivalently referred to as a "protein-protein complex." A complex may also refer to an antibody bound to its corresponding antigen. Complexes of particular interest in the invention are protein-protein complexes and antibody-antigen complexes. As noted above, various types of noncovalent interactions may contribute to antibody binding of antigen, including electrostatic threes, hydrogen bonds, van der Waals forces, and hydrophobic interactions. The relative importance of each of these depends on the structures of the binding site of the individual antibody and of the antigenic determinant. The strength of the binding between a single combining site of an antibody and an epitope of an antigen, which can be determined experimentally by equilibrium dialysis (e.g. Abbas et al (cited above)), is called the affinity of the antibody. The affinity is commonly represented by a dissociation constant ($K_d$), which describes the concentration of antigen that is required to occupy the combining sites of half the antibody molecules present in a solution of antibody. A smaller $K_d$ indicates a stronger or higher affinity interaction, because a lower concentration of antigen is needed to occupy the sites. For antibodies specific for natural antigens, the $K_d$ usually varies from about $10^{-7}$ M to $10^{-11}$ M. Serum from an immunized individual will contain a mixture of antibodies with different affinities for the antigen, depending primarily on the amino acid sequences of the CDRs.

"Ligand" means a compound that hinds specifically and reversibly to another chemical entity to form a complex. Ligands include, but are not limited to, small organic molecules, peptides, proteins, nucleic acids, and the like. Of particular interest are protein-ligand complexes, which include protein-protein complexes, antibody-antigen complexes, receptor-ligand complexes, enzyme-substrate complexes, and the like.

"Phage display" is a technique by which variant polypeptides are displayed as fusion proteins to at least a portion of a coat protein on the surface of phage, e.g., filamentous phage, particles. A utility of phage display lies in the fact that large libraries of randomized protein variants can be rapidly and efficiently selected for those sequences that hind to a target molecule with high affinity. Display of peptide and protein libraries on phage has been used for screening millions of polypeptides for ones with specific binding properties. Polyvalent phage display methods have been used for displaying small random peptides and small proteins through fusions to either gene III or gene VIII of filamentous phage. Wells and Lowman, *Curr. Opin. Struct. Biol.,* 3:355-362 (1992), and references cited therein. In monovalent phage display, a protein or peptide library is fused to a gene III or a portion thereof, and expressed at low levels in the presence of wild type gene III protein so that phage particles display one copy or none of the fusion proteins. Avidity effects are reduced relative to polyvalent phage so that selection is on the basis of intrinsic ligand affinity, and phagemid vectors are used, which simplify DNA manipulations, Lowman and Wells, *Methods: A companion to Methods in Enzymology,* 3:205-0216 (1991).

"Phagemid" means a plasmid vector having a bacterial origin of replication, e.g., Co1E1, and a copy of an intergenic region of a bacteriophage. The phagemid may be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids, contain a phage coat protein gene or fragment thereof linked to a heterologous polypeptide gene as a gene fusion such that the heterologous polypeptide is displayed on the surface of the phage particle.

"Phage" or "phage vector" means a double stranded replicative form of a bacteriophage containing a heterologous gene and capable of replication. The phage vector has a phage origin of replication allowing phage replication and phage particle formation. The phage is preferably a filamentous bacteriophage, such as an M13, f1, fd, Pf3 phage or a derivative thereof, or a lambdoid phage, such as lambda, 21, phi80, phi81, 82, 424, 434, etc., or a derivative thereof.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Dieffenbach, editor, PCR Primer: A Laboratory Manual, $2^{nd}$ Edition (Cold Spring Harbor Press, New York, 2003).

"Polypeptide" refers to a class of compounds composed of amino acid residues chemically bonded together by amide linkages with elimination of water between the carboxy group of one amino acid and the amino group of another amino acid. A polypeptide is a polymer of amino acid residues, which may contain a large number of such residues. Peptides are similar to polypeptides, except that, generally, they are comprised of a lesser number of amino acids. Peptides are sometimes referred to as oligopeptides. There is no clear-cut distinction between polypeptides and peptides. For convenience, in this disclosure and claims, the term "polypeptide" will be used to refer generally to peptides and polypeptides. The amino acid residues may be natural or synthetic.

"Protein" refers to a polypeptide, usually synthesized by a biological folded into a defined three-dimensional structure. Proteins are generally from about 5,000 to about 5,000,000 daltons or more in molecular weight, more usually from about 5,000 to about 1,000,000 molecular weight, and may include posttranslational modifications, such acetylation, acylation, ADP-ribosylation, amidation, disulfide bond formation, farnesylation, demethylation, formation of covalent cross-links, formation of cystine, glycosylation, hydroxylation, iodination, methylation, myristoylation, oxidation, phosphorylation, prenylation, selenoylation, sulfation, and ubiquitination, e.g. Wold, F., Post-translational Protein Modifications; Perspectives and Prospects, pgs. 1-12 in Post-translational Covalent Modification of Proteins, B. C. Johnson, Ed., Academic Press, New York, 1983. Proteins include, by way of illustration and not limitation, cytokines or interleukins, enzymes such as, e.g., kinases, proteases, galactosidases and so forth, protamines, histones, albumins, immunoglobulins, scleroproteins, phosphoproteins, mucoproteins, chromoproteins, lipoproteins, nucleoproteins, glycoproteins, T-cell receptors, ligand/hormone receptors, proteoglycans, and the like.

"Specific" or "specificity" in reference to the binding of one molecule to another molecule, such as a labeled target sequence for a probe, means the recognition, contact, and formation of a stable complex between the two molecules, together with substantially less recognition, contact, or complex formation of that molecule with other molecules. In some embodiments, "specific" in reference to the binding of a first molecule to a second molecule means that to the extent the first molecule recognizes and forms a complex with another molecule in a reaction or sample, it forms the largest number of the complexes with the second molecule. Preferably, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak noncovalent chemical interactions, such as Van der Waal forces, hydrogen bonding, base-stacking interactions, ionic and hydrophobic interactions, and the like, dominate the interaction of the molecules.

"Wild type" or "reference" or "pre-existing" in reference to a binding compound are used synonymously to mean a compound which is being analyzed or improved in accordance with the method of the invention. That is, such a compound serves as a starting material from which variant polypeptides are derived through the introduction of mutations. A "wild type" sequence for a given protein is usually the sequence that is most common in nature, but the term is used more broadly here to include compounds that have been engineered. Similarly, a "wild type" gene sequence is typically the sequence for that gene which is most commonly found in nature, but the usage here includes genes that may have been engineered from a natural compound, e.g. a gene which has been engineered to consist of bacterial codons even though it encodes a human protein. Mutations may be introduced into a "wild type" gene (and thus the protein it encodes) through any available process, e.g. site-specific mutation, insertion of chemically synthesized segments, or other conventional means. The products of such processes are "variant" or "mutant" forms of the original "wild type" protein or gene. Exemplary reference (or wild type or pre-existing) sequences include antibody-targeted drugs or antibody-based drugs such as adalimumab (Humira), bevacizumab (Avastin), cetuximab (Erbitux), efalizumab (Raptiva), infliximab (Remicade), panitumumab (Vectubix), ranibuzumab (Lucentis), rituximab (Rituxan), trastuzumab (Herceptin), and the like.

What is claimed is:

1. A method of improving a predetermined characteristic of a protein binding site, the method comprising the steps of:
- synthesizing a single substitution library for each of a plurality of domains of a protein binding site, wherein each member of a single substitution library has a nucleotide sequence that encodes amino acid changes at a single amino acid position of its associated domain and that overlaps a nucleotide sequence of at least one member of a different single substitution library, and wherein the domains of the protein binding site are singlely substituted at from 1 to 250 amino acid positions;
- expressing separately each member of each single substitution library as a pre-candidate protein;
- incubating in a reaction mixture under binding conditions the pre-candidate proteins of each single substitution library with target molecules;
- washing the target molecules so that pre-candidate proteins having an affinity less than a predetermined affinity dissociate;
- forming a selected library for each domain of the protein from members of each substitution library which encode pre-candidate proteins that remain bound to the target molecules;
- shuffling members of the selected libraries in a PCR to produce a combinatorial shuffled library;
- expressing members of the shuffled library as candidate proteins;
- incubating in a reaction mixture wider binding conditions the candidate proteins with target molecules;
- washing the target molecules so that candidate proteins having an affinity less than a predetermined affinity dissociate; and
- isolating members of the shuffled library which encode candidate proteins which have an affinity to the target molecules greater than or equal to the predetermined affinity.

2. The method of claim 1 wherein said binding site is that of an antibody or an antibody fragment expressed by a protein display system.

3. The method of claim 2 wherein said protein display system is a yeast display system, a mammalian display system, a bacterial display system, an insect cell display system or a phage display system.

4. The method of claim 3 wherein said protein display system is a phage display system.

5. The method of claim 1 wherein said plurality of domains covers a contiguous amino acid sequence of said protein.

6. The method of claim 1 wherein said predetermined affinity is an affinity of a reference compound to said target molecules.

7. The method of claim 6 wherein said pre-candidate proteins of each of said single substitution libraries is treated with a chemical or physical condition selected from the group consisting of heat, low pH, high pH and protease activity.

8. The method of claim 7 wherein said heat treatment of said pre-candidate proteins comprises exposing said pre-candidate proteins to a temperature in the range of from 40-70° C.

9. The method of claim 7 wherein said low pH treatment of said pre-candidate proteins comprises exposing said pre-candidate proteins to a pH in the range of from 1-4.

10. The method of claim 7 wherein said high pH treatment of said pre candidate proteins comprises exposing said pre-candidate proteins to a pH in the range of from 9-13.

11. The method of claim 7 wherein said protease activity treatment of said pre-candidate proteins comprises exposing said pre-candidate proteins to a protease selected from the group consisting of a serum protease, a trypsin, a chymotrypsin, and a cathepsin.

12. The method of claim 1 wherein said predetermined characteristic is cross-reactivity with one or more selected substances, wherein said target molecules comprise the one or more selected substances, and wherein said step of combining said pre-candidate proteins with said target molecules includes depleting from said reaction mixture pre-candidate proteins binding to the one or more selected substances.

13. The method of claim 1 wherein said domains are singlely substituted at from 10 to 250 amino acid positions.

14. The method of claim 1 wherein said plurality is in the range of from 3 to 30.

* * * * *